United States Patent [19]

Taylor et al.

[11] Patent Number: 5,055,678
[45] Date of Patent: Oct. 8, 1991

[54] METAL SURFACES FOR SAMPLE ANALYZING AND IONIZING APPARATUS

[75] Inventors: Dennis M. Taylor, Santa Clara County, Calif.; Jonathan W. Amy, Tippecanoe County, Ind.; George C. Stafford, Jr., Santa Clara County, Calif.

[73] Assignee: Finnigan Corporation, San Jose, Calif.

[21] Appl. No.: 487,592

[22] Filed: Mar. 2, 1990

[51] Int. Cl.$^5$ .............................................. H01J 49/26
[52] U.S. Cl. .................................... 250/291; 250/292
[58] Field of Search ........................ 250/281, 291, 292

[56] References Cited

U.S. PATENT DOCUMENTS 4,359,661 11/1982 Mitrofanov ........................... 313/93
4,779,107 10/1988 Weisfield et al. ................... 346/159

Primary Examiner—Bruce C. Anderson
Attorney, Agent, or Firm—Flehr, Hohbach, Test, Albritton & Herbert

[57] ABSTRACT

A chromium or oxidized chromium surface for use in sample analyzing and ionizing apparatus, such as an ion trap or ionization chamber, which does not degrade or decompose a sample in contact with the surface.

11 Claims, 1 Drawing Sheet

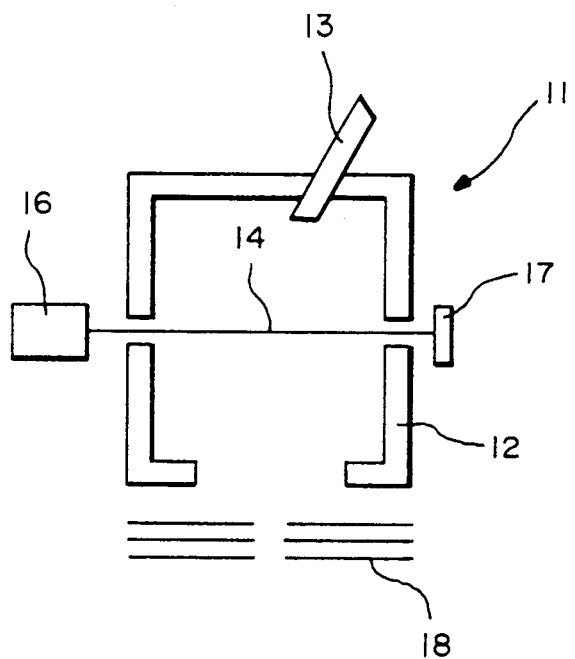
FIG.—1
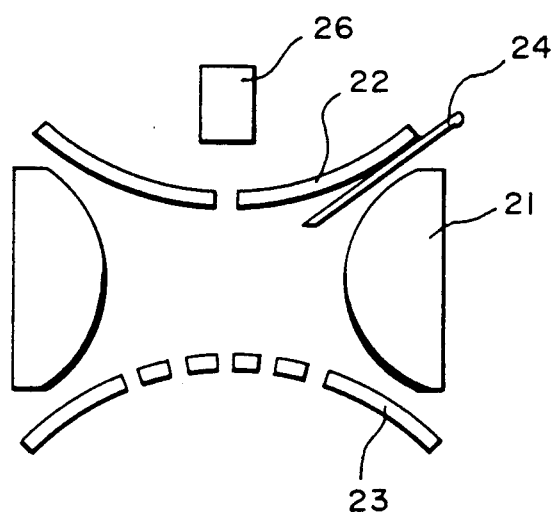
FIG.—2

METAL SURFACES FOR SAMPLE ANALYZING AND IONIZING APPARATUS

BRIEF DESCRIPTION OF THE INVENTION

This invention relates to metal surfaces for sample analyzing and ionizing apparatus, and more particularly to surfaces which contact samples in ionization chambers, chromatographic apparatus and ion traps.

BACKGROUND OF THE INVENTION

Hot metal surfaces, as found in chambers used to perform ionization in mass spectrometers, are known to interact with certain chemical species to decompose said species before ionization takes place. For instance, chlorinated compounds, such as the pesticides Lindane and Methoxychlor, will decompose in such a way that the mass spectrum produced following ionization will be quite different from that of a standard sample, run on an instrument with a chamber having deactivated surfaces. Other classes of compounds, such as the pesticide Parathion, will also show decomposition before ionization, with the resulting spectrum being of a different substance. These chemical degradations are of particular importance when performing quantitative analysis of low levels of materials, such as is done in gas chromatograph/mass spectrometer (GC/MS) analysis of pesticide residues, drug residues and metabolites, or trace analysis of organic compounds.

In addition to sample degradation, active metal surfaces will also influence chromatographic peak shape. Materials eluting from a gas chromatographic column impinging on a surface may stick to the surface in such a way that the shape of a symmetrical peak is changed to one with a long tail.

Similar sample degradation problems have also been found in heated sample injectors, metal transfer lines and detectors of gas chromatographs.

One way of minimizing these effects has been to treat the metal surfaces with some form of passivating agent to cover up or destroy active surface sites. An example is the use of alkylchlorosilanes and similar types of silynizing agents, to treat injectors, chromatographic columns, transfer lines, and detectors in gas chromatography.

Such treatments of ionization chamber parts in mass spectrometry will deactivate metal surfaces, preventing sample degradation, but the materials used have sufficient vapor pressure to produce organic material in the gas phase within the volume of the ionization chamber. Such material is ionized along with the sample, producing a high chemical background within the mass spectrum of the sample. Such background makes compound identification and quantitative analysis extremely difficult.

Surfaces of electropolished stainless steel have been found to give variable results, and not to be stable with time in terms of sample degradation. Hot chamber surfaces coated with gold, nickel or rhodium show degradation of samples of pesticides, such as Methoxychlor, Lindane and Parathion, of drugs and metabolites.

OBJECTS AND SUMMARY OF THE INVENTION

It is an object of this invention to provide a metal surface for use in sample analyzing ionizing apparatus which does not degrade or decompose a sample in contact therewith.

The foregoing object is achieved by providing chromium or oxidized chromium surfaces which are in contact with the sample in a sample confinement structure such as an ion trap or ionization chamber.

BRIEF DESCRIPTION OF THE FIGURES

The foregoing and other objects of this invention will be more clearly understood from the following description, taken in connection with the accompanying drawings, of which:

FIG. 1 schematically shows an ionizing chamber for ionizing samples and providing ions to an associated mass analyzer.

FIG. 2 schematically shows an ion trap into which a sample is introduced, ionized, and the ions trapped.

DESCRIPTION OF PREFERRED EMBODIMENTS

FIG. 1 shows a typical ionization chamber 11 having metal walls 12 into which the sample to be analyzed is introduced by an injection tube 13. The sample is ionized by an electron beam 14 which is projected through the ionizing chamber by an electron source 16 to a collector 17. Ions are drawn from the chamber by the lens assembly 18 which directs the ions to an associated analyzing apparatus such as a mass spectrometer.

It is apparent that although an electron impact ionization chamber is disclosed, the present invention is also applicable to other types of ionizing chambers, such as chemical ionization chambers.

Generally in the prior art, the chamber walls are formed of stainless steel or other suitable metal. As described above, such surfaces decompose and degrade the sample. We have discovered that by covering the metal surfaces of the chamber in contact with the sample with a layer of chromium, the hot metal surfaces do not decompose or degrade compounds such a as pesticides Methoxychlor, Lindane and Parathion, or any other compounds found in the analysis of drugs, metabolites and trace analysis. Such chamber wall lining does not leave a volatile residue and does not produce a chemical background in the mass spectrum of samples ionized in such a chamber.

The chromium surface can be formed by chrome-plating the walls and surfaces of the chamber walls or trap which come in contact with the sample, by making the walls entirely of chromium, or by employing walls made of an alloy including chromium, which can be chemically or physically treated to leave a substantially chromium surface. It is believed that the chromium or chromium oxide formed on the surface provides the stable and inactive surface.

This invention is not only applicable to ionization chambers, but also to ion traps and other containments that come in contact with the samples which may be degraded or decomposed by metal surfaces. In FIG. 2, a well-known ion trap is shown. Operation of such traps are well-known in the art. Reference is made to U.S. Pat. No. 4,540,884 for a description of the operation of an ion trap for analysis of a sample. The ion trap includes a ring electrode 21 and end caps 22 and 23, which define an ion volume. The sample is introduced into the ion volume via a tube or injector 24 and is ionized by an electron beam projected by the electron source 26.

The same decomposition and degradation problems as described above are encountered in an ion trap. We have found that when the trap wall surfaces which are in contact with the sample include chromium or chromium oxide; that is, are chrome-plated or otherwise deposited, made of chrome or treated as described above, the ion trap operates satisfactorily to obtain mass spectra of pesticides, drugs, and metabolites and the like, without decomposition or degradation.

It is apparent that the advantages of chrome surfaces as described above in connection with ionizing chambers and ion traps are also applicable to other surfaces which may come in contact with effluent from chromatographic columns, heated sample injectors, metal transfer lines and detectors for gas chromatographs.

What is claimed is:

1. In a sample handling apparatus of the type which includes an ion trap which holds a sample, the improvement comprises providing chromium metal surfaces at the interface between the sample and the ion trap to minimize decomposition or degradation of the sample.

2. Apparatus as in 1 in which said chromium surface is a plated surface.

3. Apparatus as in 1 in which said chromium is a deposited surface.

4. In a sample handling apparatus of the type which includes an ionization chamber which holds a sample and sample ions, the improvement comprises providing chromium metal surfaces at the interface between the sample and the ionization chamber to minimize decomposition or degradation of the sample and sample ions in the ionization chamber.

5. Apparatus as in claim 4 in which said chromium surface is a plated surface.

6. Apparatus as in claim 4 in which said chromium is a deposited surface.

7. In a sample handling apparatus of the type which includes sample ion containment means, the improvement comprising chromium metal surfaces at the interface between the sample ions and the containment means whereby to minimize the decomposition or degradation of the sample ions in the containment means.

8. Apparatus as in claim 7 in which said containment means comprises an ionization chamber.

9. Apparatus as in claim 7 in which said containment means comprises an ion trap.

10. Apparatus as in any one of claims 7, 8, or 9 in which said chromium surface is a plated surface.

11. Apparatus as in any one of claims 7, 8, or 9 in which said chromium surface is a deposited surface.

* * * * *

UNITED STATES PATENT AND TRADEMARK OFFICE
CERTIFICATE OF CORRECTION

PATENT NO. : 5,055,678

DATED : October 8, 1991

INVENTOR(S) : Dennis M. Taylor, Jonathan W. Amy, George C. Stafford

It is certified that error appears in the above-identified patent and that said Letters Patent is hereby corrected as shown below:

Column 1, line 68 after "analyzing" insert --and--.

Column 2, line 40, delete "a".

Column 2, line 40, after "as" insert --the--.

Signed and Sealed this

Second Day of March, 1993

Attest:

STEPHEN G. KUNIN

*Attesting Officer*　　　　*Acting Commissioner of Patents and Trademarks*